United States Patent [19]
Kassel et al.

[11] Patent Number: 6,066,848
[45] Date of Patent: May 23, 2000

[54] PARALLEL FLUID ELECTROSPRAY MASS SPECTROMETER

[75] Inventors: Daniel B. Kassel, Del Mar; Tao Wang; Lu Zeng, both of San Diego, all of Calif.

[73] Assignee: CombiChem, Inc., San Diego, Calif.

[21] Appl. No.: 09/185,450

[22] Filed: Nov. 3, 1998

Related U.S. Application Data

[60] Provisional application No. 06/088,665, Jun. 9, 1998.

[51] Int. Cl.$^7$ .................................................... H01J 49/10
[52] U.S. Cl. ........................................... 250/288; 250/285
[58] Field of Search ............................... 250/288, 288 A, 250/285

[56] References Cited

U.S. PATENT DOCUMENTS

| | | | |
|---|---|---|---|
| 2,534,181 | 12/1950 | Roberts | 73/422 |
| 3,802,782 | 4/1974 | Natelson | 356/180 |
| 4,004,150 | 1/1977 | Natelson | 250/328 |
| 4,051,731 | 10/1977 | Bohl et al. | 73/422 |
| 4,840,074 | 6/1989 | Jessop | 73/864.81 |
| 5,288,514 | 2/1994 | Ellman | 427/2 |
| 5,449,902 | 9/1995 | Onishi et al. | 250/288 |
| 5,668,370 | 9/1997 | Yano et al. | 250/288 |
| 5,756,994 | 5/1998 | Bajic | 250/288 |

FOREIGN PATENT DOCUMENTS

| | | | |
|---|---|---|---|
| WO 98/56028 | 12/1998 | WIPO | H01J 49/04 |
| WO 99/13492 | 3/1999 | WIPO | . |

OTHER PUBLICATIONS

Xue et al., "Multichannel Microchip Electrospray Mass Spectrometry", Analytical Chemistry, vol. 69, No. 3, Feb. 1, 1997, pp. 426–430.

De Biasi, Verner et al., High Throughput Liquid Chromatography/Mass Spectrometric Analyses using a Novel Multiplexed Electrospray Interface, *Rapid Communications In Mass Spectrometry*, 13, 1–4 (1999).

Printed Materials from http://www.micromass.co.uk — Press Centre—Pittcon '99 Press Releases: Announcing the World's First Parallel LC–MS! ...Micromass'LCT™ with MUX–Technology™(with image) (/pprl.htm).

Printed Materials from http://www.micromass.co.uk —Drug Discovery (with image) (/pharm4.htm).

Printed Materials from http//www.micromass.co.uk —News in brief (with image) (/asmsag.htm).

Printed Materials from http://www.micromass.co.uk — Press Centre —Pittcon '99 Press Releases: New—Products: (/ppr.htm).

MicroMass Brochure: LCT™ with MUX–technology™ shows excellent chromatographic integrity for all four channels with negligible inter–channel cross–talk.

(List continued on next page.)

*Primary Examiner*—Jack Berman
*Attorney, Agent, or Firm*—Townsend & Townsend & Crew LLP

[57] ABSTRACT

A method of analyzing each of a plurality of fluid samples (11–16), comprising, simultaneously spraying a plurality fluid samples (11–16) from electrospray needle array (20) towards mass spectrometer (50); positioning blocking device (40) to block all but one (32–34) of fluid samples (31–34) from reaching mass spectrometer (50); moving electrospray needle array (20) and blocking device (40) relative to one another to permit at least two of the plurality of fluid samples (31, 32) to reach mass spectrometer (50) one at a time; and analyzing the mass spectrum of fluid samples (31, 32, 33, 34) sequentially reaching mass spectrometer (50). A system for analyzing the composition of each of a plurality of fluid samples (31–34), comprising, mass spectrometer (50); multi-head electrospray needle array (20) for spraying fluid samples (31–34) towards mass spectrometer (50); and blocking device (40) positioned between electrospray needle array (20) and mass spectrometer (50), blocking device (40) dimensioned to block all but one (32–34) of fluid sample electrosprays (31–34) from reaching mass spectrometer (50).

28 Claims, 9 Drawing Sheets

OTHER PUBLICATIONS

R. Loo, H. Udseth, and R. Smith, "Evidence of Charge Inversion in the Reaction of Singly Charged Anions with Multiply Charged Macroions", The Journal of Physical Chemistry, vol. 95, No. 17, 1991, pp. 6412–6415.

A. Rulison and R. Flagan, "Scale–Up Electrospray Atomization Using Linear Arrays of Taylor Cones", Rev. Sci. Instr., vol. 64, No. 3, Mar. 1993, pp. 683–686.

R. Kostiainen and A. Bruins, "Effect of Multiple Sprayers on Dynamic Range and Flow Rate Limitations in Electrospray and Ionspray Mass Spectrometry", Journal of Mass Spectrometry, 1994, pp. 549–558.

"JMS Letters", Journal of Mass Spectrometry, vol. 32, pp 247–250, 1997.

P. Coffey, "Parallel Purification for Combinatorial Chemistry", Laboratory Automation News, vol. 2, No. 2, May 1997, pp. 6–14.

L. Zeng, L. Burton, K. Yung, B. Shushan, D.B. Kassel, "Automated Analytical/Preparative High–Performance Liquid Chromatography–Mass Spectrometry System for the Rapid Characterization and Purification of Compound Libraries", Journal of Chromatography A., 794 (1998) pp. 3–13.

R. Stevenson, "The World of Separation Science: LabAutomation '98 Features Latest Developments in Combinatorial Chemistry and High–Throughput Screening", American Laboratory News, Mar. 1998, 7 pages.

L. Zeng, X. Wang, T. Wang, and D. B. Kassel, "New Developments in Automated PrepLCMS Extends the Robustness and Utility of the Method for Compound Library Analysis and Purification", Combinatorial Chemistry and High Throughput Screening, published Jun. 1, 1998 pp. 1–31.

PARALLEL FLUID ELECTROSPRAY MASS SPECTROMETER

This application is a Continuation of application Ser. No. 60/088,665, filed on Jun. 9, 1998, which is incorporated herein by reference for all purposes.

TECHNICAL FIELD

The present invention relates to mass spectrometry, high performance liquid chromatography (HPLC), and combinatorial chemistry.

BACKGROUND OF THE INVENTION

The advent of combinatorial chemistry, and more specifically, high throughput parallel synthesis, has placed greater and greater demands on compound analysis and purification tools. Combinatorial synthesis is used to efficiently generate large numbers of unique compounds. Analysis of the composition of these samples can be done by high performance liquid chromatography (hereafter "HPLC") in combination with mass spectrometry (hereafter "MS"), whereby each fluid sample is separated into its various components as they are partitioned between the solid sorbent packing material of the chromatographic column and the carrier mobile phase. In such columns, each of the different component compounds found in each fluid sample will interact differently with the solid sorbent material contained within the chromatographic column and will accordingly take different amounts of time to pass through and be eluted out of the exit end of the column.

Typically, such liquid chromatography methods are performed in conjunction with ultraviolet (UV) or mass spectrometry-based analysis techniques as a means of identifying and isolating desired component compounds in the various fluid samples by determining exactly when such a desired component compound is eluted from the exit end of the column. Accordingly, liquid chromatography-mass spectrometry systems can be used to purify fluid samples by first separating a fluid sample into its component compounds and then collecting only the desired component compounds found therein. Unfortunately, these systems suffer from several disadvantages.

First, liquid chromatography-mass spectrometry systems have required that each fluid sample be analyzed in sequence. Parallel analysis of different fluid samples is not possible, for reasons which will be explained. Accordingly, the efficiency of combinatorial library analysis and purification is limited by the maximum speed at which the high performance liquid chromatograph-mass spectrometer (HPLC/MS) system can sequentially analyze each one of the various fluid samples so produced.

Parallel analysis of different fluid samples is not possible with existing HPLC/MS systems because the mass spectrometer will simply generate a mass spectrum reading corresponding to all of the fluid being electrosprayed or otherwise received therein at any particular moment in time. As such, the mass spectrometer cannot distinguish between parallel electrosprays of different fluid samples simultaneously received therein. Instead, should two or more parallel electrosprays enter the mass spectrometer at the same time, the mass spectrometer would simply analyze all of the various compounds found in all of the various simultaneously-received electrosprays. As such, it is not possible for the mass spectrometer to determine from which of a plurality of simultaneously-received electrosprays a particular sensed fluid compound was present.

Moreover, when performing HPLC, time is required to separate each fluid sample into its component compounds. The time required to separate each of the fluid samples must then be added together when sequentially performing liquid chromatography on a number of different fluid samples. Accordingly, a rather time-consuming process is required in which each fluid sample must be sequentially subjected to HPLC/MS.

Further, when spraying the samples into a mass spectrometer, it is preferable that as small a portion of the sample as possible be diverted into the mass spectrometer, thus conserving the majority of the fluid samples for isolation and fraction collection.

SUMMARY OF THE INVENTION

The present invention provides methods and systems for analyzing the composition of a plurality of fluid samples and more particularly for analyzing the mass spectrum of a plurality of fluid samples separated into component compounds by liquid chromatography and electrosprayed into a mass spectrometer. An important advantage of the present invention is that it allows simultaneous mass spectral analysis of each of the plurality of fluid samples using only a single mass spectrometer. Accordingly, the present invention requires substantially less time to analyze the composition of a plurality of fluid samples as compared to existing systems in which samples are analyzed sequentially by HPLC/MS. Instead, the present invention is able to distinguish between each of a plurality of fluid samples simultaneously electrosprayed from parallel liquid chromatography columns towards a mass spectrometer such that the mass spectra associated with each fluid sample can be reliably determined, as follows.

In a preferred method, a plurality of fluid samples is simultaneously separated by parallel liquid chromatography columns and are then simultaneously electrosprayed towards an entrance orifice of a mass spectrometer. A blocking device having an aperture passing therethrough is positioned so as to block all but one of the fluid samples from passing into the entrance orifice of the mass spectrometer at any moment in time. In a preferred aspect of the method, the blocking device and an array of electrospray needles connected to the columns are moved relative to one another so as to permit each effluent of the plurality of chromatographically-separated fluid samples to sequentially pass through the aperture in the blocking device and into the entrance orifice of the mass spectrometer one at a time. In particular, a rotating blocking device is moved relative to a plurality of stationary, equally spaced (i.e., arrayed) electrospray needles. The mass spectrometer thus analyzes each one of the chromatographically-separated fluid sample electrosprays received therein in turn. By knowing the position and speed of movement of the blocking device relative to the electrospray needles, it is then possible to determine which fluid sample spray has passed into the mass spectrometer and is being analyzed at any particular moment in time. Accordingly, the mass spectrum of each electrosprayed fluid sample can be separately determined and distinguished from one another, regardless of the fact that each of the plurality of fluid samples are electrosprayed simultaneously out the exit ends of parallel electrospray needles. Preferably, the blocking device is moved relative to the electrospray needles in a repetitive or cyclical manner such that each one of the fluid samples enters the mass spectrometer in turn again and again during the course of an LC/MS analysis.

In a preferred aspect of the method, positioning and moving the blocking device comprises positioning a rotating disc between the electrospray needles and the mass spectrometer. The disc has a aperture passing therethrough which is dimensioned so as to permit only one of the plurality of fluid sample electrosprays to pass therethrough and enter the mass spectrometer. In this preferred aspect, the fluid samples are simultaneously and continuously electrosprayed from parallel electrospray needles. The disc is then rotated such that each of the fluid sample electrosprays pass through the aperture and enter the mass spectrometer in turn. By continuously rotating the disc around and around, each of the fluid sample electrosprays will be analyzed again and again in a repeating pattern at a number of moments in time.

As was stated above, each fluid sample is separated into its component compounds as it passes along through a chromatographic column, (since different compounds in each fluid sample take different amounts of time to pass therethrough). Therefore, different component compounds in each fluid sample will be electrosprayed out of the end of each electrospray needle and be analyzed by the mass spectrometer at different moments in time. Accordingly, a varying mass spectrum reading will be generated for each of the plurality of fluid sample electrosprays over time.

Preferably, the fluid samples are simultaneously electrosprayed from an array of electrospray needles in trajectories which are parallel to one another. More preferably, the fluid sample electrosprays are each targeted at locations on the rotating disc which are generally equidistant from the center of the disc and which each align with the center of the aperture of the disc as the disc is rotated. Accordingly, rotation of the disc moves the aperture relative to the array of parallel electrospray needles such that each one of the fluid samples sequentially passes through the aperture in the disc and is analyzed by the mass spectrometer in turn.

In another preferred aspect of the method, the blocking device positioned between the electrospray needle array and the mass spectrometer comprises a plurality of high speed valves or shutters, (with each valve or shutter being dedicated to a particular electrospray needle), which open and close one after another in sequence to permit each of the fluid samples to be electrosprayed into the mass spectrometer and analyzed in turn.

In yet another preferred aspect of the method, the plurality of fluid samples are electrosprayed into the mass spectrometer one after another from respective electrospray needles in an array of electrospray needles, each connected to individual columns.

In any of the above preferred aspects of the present method, the mass spectrometer preferably generates a continuous mass spectrum reading over a period of time. A mass spectrum reading for any particular fluid sample can be determined by sampling the continuous mass spectrum reading at the moments in time which correspond to when that particular fluid sample is being analyzed in the mass spectrometer. The exact moments in time when each fluid sample enters the mass spectrometer and is analyzed is determined by knowing the position of the aperture with respect to the fluid sample electrosprays over time. The mass spectrum reading of samples for any particular fluid sample will be expected to vary over time since each of the sample's component compounds will be eluted from the end of the column at different times.

The preferred method also comprises a method of purifying each of the plurality of electrosprayed fluid samples. This method of purifying is ideally suited for use with a quadrupole mass spectrometer which detects the presence of positively or negatively charged gas phase ions corresponding to a particular molecular mass in a fluid sample corresponding to the voltage level applied across the quadrupole rods. By adjusting the voltage across the quadrupole rods to different levels, the mass spectrometer can be adjustably set to detect the presence of various molecular masses in the ionized sample.

In the preferred method of purifying a fluid sample, each of the plurality of fluid sample electrosprays are directed into the mass spectrometer using any aspect of the above described method. Concurrently, as each fluid sample is analyzed in the mass spectrometer, the voltage across the mass spectrometer's quadrupole rods is incrementally stepped to a voltage level which corresponds to the molecular mass of a desired reaction product expected to be found in that particular fluid sample. Each fluid sample is then analyzed in turn at a voltage level corresponding to the desired reaction product expected to be found in the fluid sample. In addition, when using a rotating disc blocking device positioned between an array of electrospray needles and a mass spectrometer, the rotation of the blocking disc is preferably synchronized with the stepping of the voltage level across the quadrupole rods such that the quadrupole rod senses the presence and concentration of the particular desired reaction product expected to be found in each fluid sample, as follows. A first fluid sample spray is analyzed at a first quadrupole rod voltage corresponding to the molecular mass of a desired reaction product expected to be found in this first fluid sample spray. The disc is then rotated such that a second fluid sample spray passes therethrough. At the time when the fluid sample being analyzed is changed, the voltage is stepped to a second voltage level such that the second sample is analyzed by the quadrupole mass spectrometer at the second voltage corresponding to the molecular mass of a desired reaction product expected to be found in the second fluid sample spray. This process is repeated such that each fluid sample is analyzed in sequence with the concentration of the desired molecular mass corresponding to each fluid sample being determined. This method offers time efficiency advantages when analyzing fluid samples electrosprayed in parallel as only the desired reaction products in the various samples are monitored. Accordingly, a complete mass spectral analysis need not be performed on each fluid sample, and hence each electrosprayed fluid sample can be sampled more frequently, permitting increased numbers of parallel columns to be simultaneously analyzed in this aspect of the present invention.

As the presence and concentration of each of the desired compounds in each of the respective fluid samples can be determined by the above method, the fluid samples can be purified with fraction collection, as follows. In a preferred aspect of sample purification, fraction collection is performed such that when a desired molecular mass, (corresponding to a desired reaction compound), is detected by the mass spectrometer to be in a sufficiently high concentration in a fluid sample spray, the flow of that fluid sample is diverted into a fraction collector. Only a small portion, (typically less than 1%), of a fluid sample passing out of a column needs to be electrosprayed into the mass spectrometer for analysis. This small portion is unrecoverable, but the remaining recoverable portion (typically over 99%), of the fluid sample can be passed directly into a fraction collector as it passes out of the end of the column. As the desired reaction compounds found in the various fluid samples will pass out of respective columns at different times, the present method comprises selective fraction collection at those moments in time when a desired reaction product appears in a sufficiently high concentration in a fluid sample. Accordingly, separate and simultaneous fraction collection of different desired reaction compounds found in the various fluid samples is achieved with each fluid sample being selectively collected at moments in time when the desired compound is being eluted from the end of the column. Accordingly, purification of each fluid sample is thus achieved by collecting the fluid sample only when the desired compound in the fluid sample is of a desirably high concentration.

The preferred method also comprises a method of analyzing each of the individual fluid sample electrosprays so as to determine their composition. In this preferred method of sample analysis, each of the plurality of fluid sample electrosprays are directed into the mass spectrometer as described herein. The present method of analyzing each fluid sample is ideally suited for use with various mass spectrometers, including quadrupole mass spectrometers and time-of-flight mass spectrometers and has the advantage that a complete fluid compositional analysis will be performed on each fluid sample, as follows.

When using a quadrupole mass spectrometer, the voltage across the quadrupole rods is preferably swept across a range of voltages for each fluid sample as each fluid sample is analyzed in turn. Each fluid sample is analyzed in turn such that a first sample is analyzed while the voltage swept across the entire voltage range, then a second sample is analyzed while the voltage again swept across the entire voltage range, etc. As such, a complete mass spectral analysis determining the composition of each fluid sample is determined by detecting the presence of various molecular masses corresponding to different quadrupole rod voltage levels as the voltage level across the quadrupole rods is swept across the voltage range. Alternatively, when using a time-of-flight mass spectrometer, (which measures the presence of different molecular masses by determining the time required for compounds having these molecular masses to pass through the flight tube of the spectrometer), the composition of each of the various fluid samples can also be analyzed in turn. An advantage of using a time-of-flight mass spectrometer is that time is not required to sweep a voltage across a range for each of the fluid sample electrosprays being analyzed by the mass spectrometer in turn, and therefore, the time required to perform a mass spectrum analysis is reduced significantly.

The present invention also provides an apparatus for analyzing a plurality of fluid samples comprising a mass spectrometer, an electrospray needle array, and a blocking device dimensioned to selectively block all but one of the plurality of fluid samples from entering the mass spectrometer. The blocking device and the electrospray needle array are moveable with respect to one another such that each of the plurality of fluid samples can be permitted to pass through the blocking device, enter the mass spectrometer, and be analyzed by the mass spectrometer in turn. In various preferred embodiments, the mass spectrometer may comprise a quadrupole mass spectrometer or a time-of-flight mass spectrometer. However, it is to understood that the present invention can comprise any type of mass spectrometer or other desired analytical device.

Additionally, it is understood that the present invention can comprise a multitude of separation methods, including, but not limited to high performance liquid chromatography, capillary electrophoresis, supercritical fluid chromatography, and capillary electrochromatography.

In one preferred aspect of the present apparatus, the blocking device comprises a rotating disc which is positioned between the electrospray needle array and the mass spectrometer. The disc preferably has an off-center aperture dimensioned to receive only one electrosprayed sample therethrough. Preferably as well, the electrospray needle array simultaneously targets each of the plurality of fluid sample electrosprays at different locations on the rotating disc, wherein these different locations and the center of the aperture are all generally equidistant from the center of the disc. Accordingly, rotation of the disc permits each fluid sample to pass therethrough in turn and enter the mass spectrometer.

A microcomputer is also preferably included for determining the moments in time when each fluid sample enters the mass spectrometer. The determination of such moments in time is based upon determining the moments in time when each fluid sample passes through the aperture of the blocking device, knowing the orientation and speed of movement of the blocking device. Accordingly, a continuous mass spectral reading which is generated by the mass spectrometer can be sampled at particular moments in time corresponding to each fluid sample. The sampling of mass spectrograph readings for each fluid sample will preferably be performed again and again as the movement of the blocking device permits each fluid sample to pass therethrough such that a mass spectral reading can be made for each fluid sample over time, changing as different component compounds in the fluid sample elute out of the end of the various columns and pass into the mass spectrometer.

As the present invention provides a very efficient system for simultaneously analyzing a plurality of electrosprays, it is ideally suited for operation in conjunction with microtiter plate reaction well array systems. Specifically, the compounds present in a plurality of reaction wells, (for example, a row or column in a standard microtiter reaction block), can be simultaneously sampled by the present system such that parallel electrospray analysis can be performed on these compounds. Moreover, fraction collection can be performed such that purified compounds can be collected in a deep or shallow well microtiter plate format.

DESCRIPTION OF THE PREFERRED EMBODIMENTS

The present invention provides methods and apparati for analyzing the composition of a plurality of fluid samples and in particular for analyzing the mass spectrum of each of a plurality of fluid samples which are separated into component compounds by methods which may include liquid chromatography, capillary electrophoresis, supercritical fluid chromatography, and electrospray ionization-mass spectrometry and are then electrosprayed or flow injected by a direct transfer line into a mass spectrometer or any other desired sample analyzer.

Figures 1, 1A:
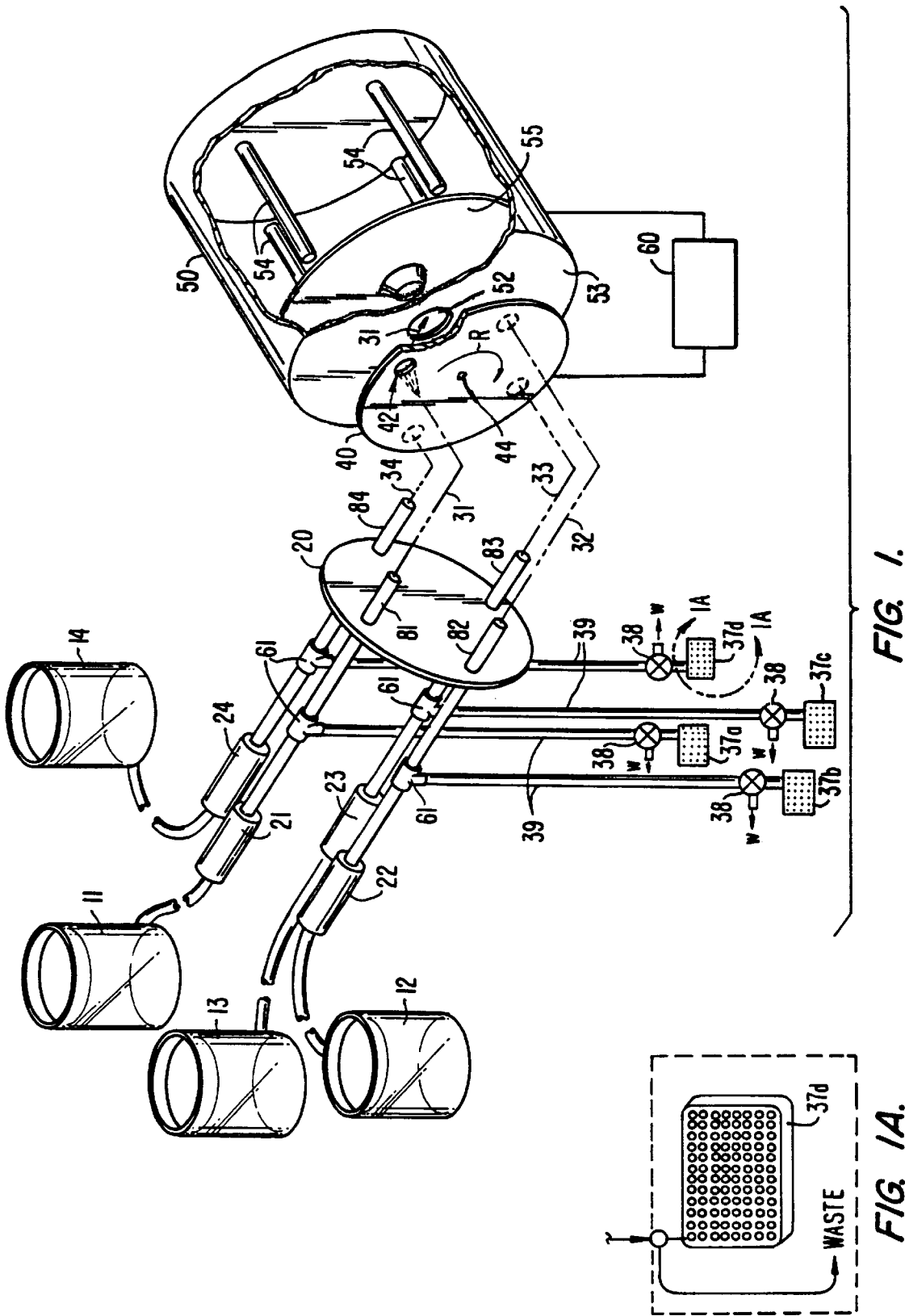
FIG. 1 is a schematic view of a first embodiment of the present invention comprising a rotating disc blocking device positioned between an electrospray needle array and a mass spectrometer.
FIG. 1A is an enlarged view of the region encompassed by line 1A—1A in FIG. 1, showing fraction collection in microtitre plate format.
Figure 2:
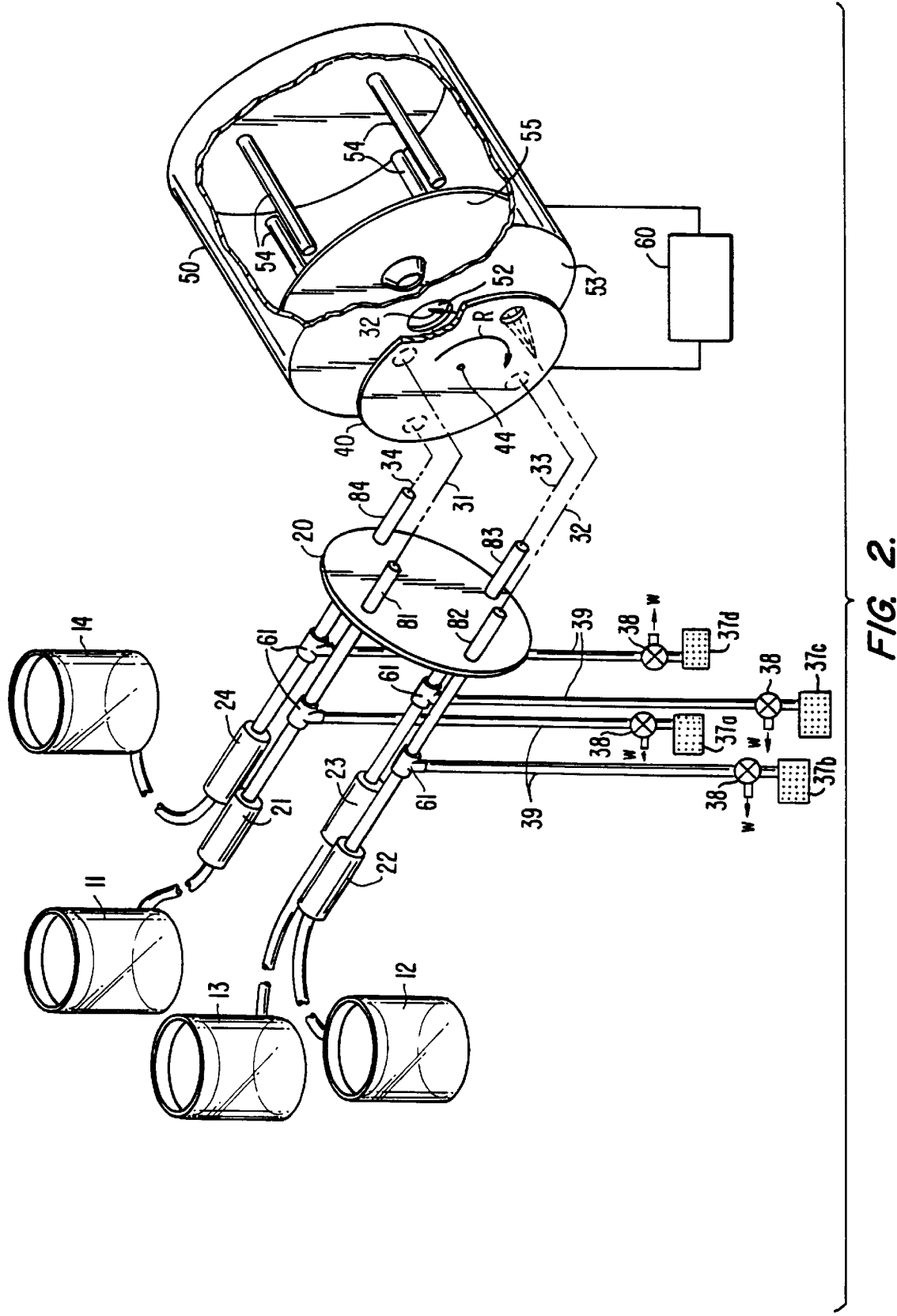
FIG. 2 is a schematic view corresponding to FIG. 1, but with the rotating disc rotated to a second position.
Figure 3:
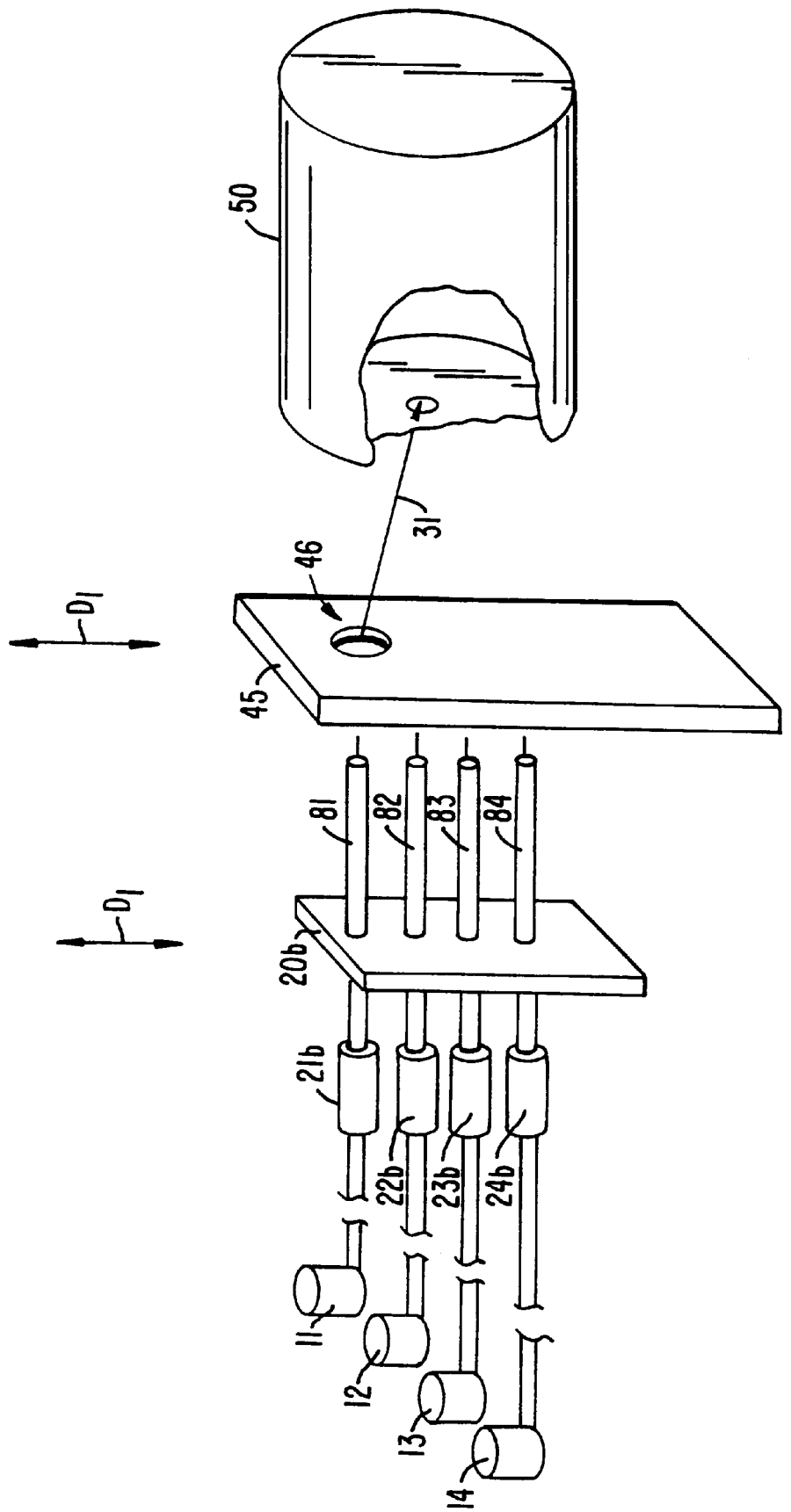
FIG. 3 is a second embodiment of the present invention comprising a sliding plate blocking device positioned between an electrospray needle array and a mass spectrometer.
Figure 4:
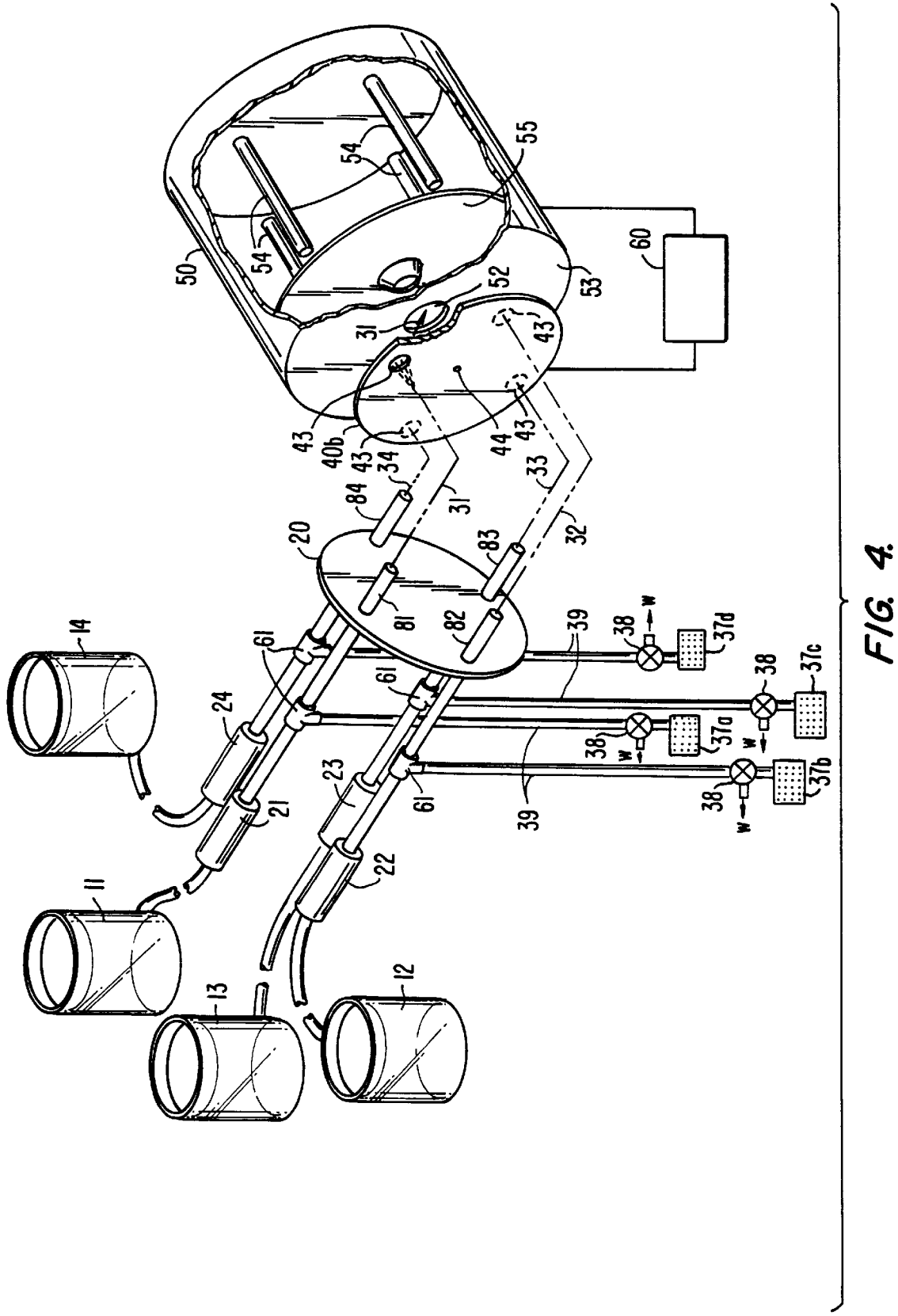
FIG. 4 is a schematic view of a third embodiment of the present invention similar to FIGS. 1 and 2, but with each column having a dedicated shuttering valve passing through a common non-rotating blocking device.
Figure 5:
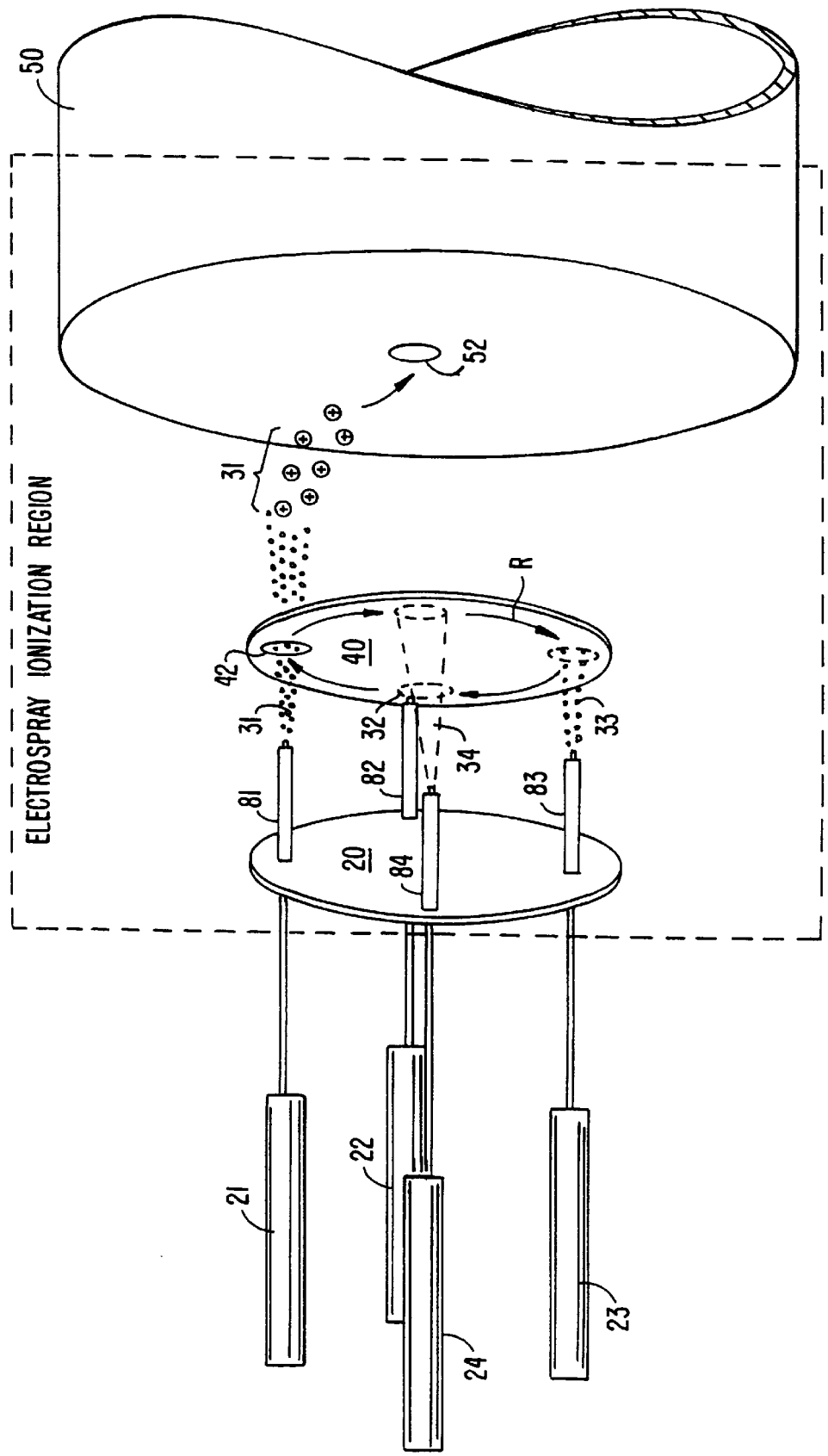
FIG. 5 is an enlarged schematic view of the electrospray ionization region of the electrospray array of FIGS. 1, 2, and 4.

In a first preferred aspect of the present invention, as is seen in FIGS. 1 and 2, a plurality of separate fluid samples 11, 12, 13, and 14, are fluidly connected to respective columns 21, 22, 23 and 24. Fluid samples 11, 12, 13 and 14 may preferably comprise fluid samples drawn from the individual wells a of a conventional microtiter plate. Columns 21, 22, 23 and 24 each may comprise high performance HPLC columns, capillary electrophoresis columns supercritical fluid chromatography columns or flow injection transfer lines. For purposes of example only, the present application hereafter describes columns 21, 22, 23 and 24 comprising high performance HPLC columns, each containing a reactive resin that facilitates separation of a fluid sample passing therethrough into its component compounds. This is accomplished as each of the various component compounds within any fluid sample will react differently with the resin and thus take different amounts of time to pass through and be eluted out of the exit end of the column.

Figure 6:
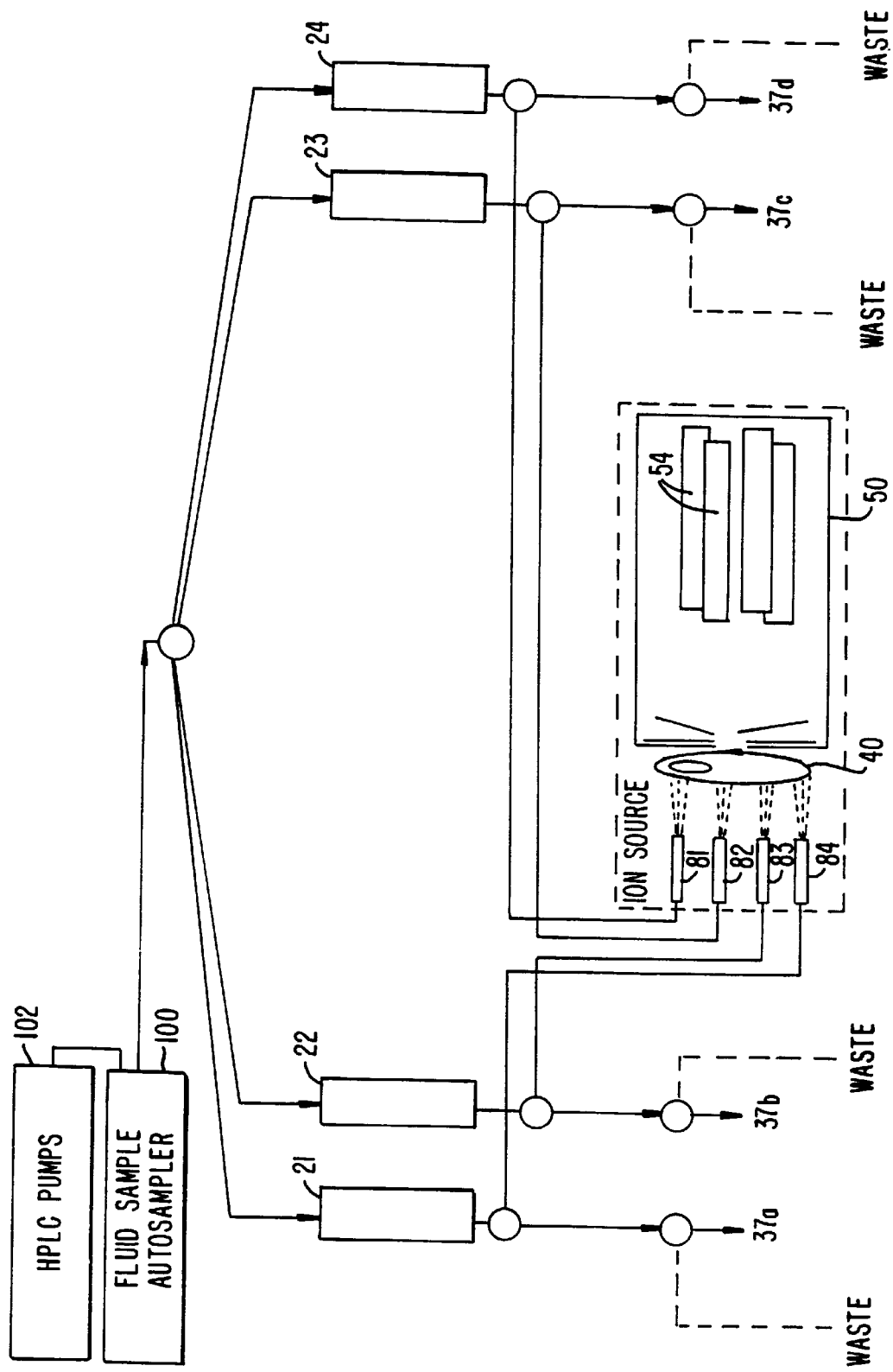
FIG. 6 is a schematic representation of the system corresponding to FIGS. 1 to 5, shown operating in conjunction with an autosampler and HPLC pumps.
Figure 7:
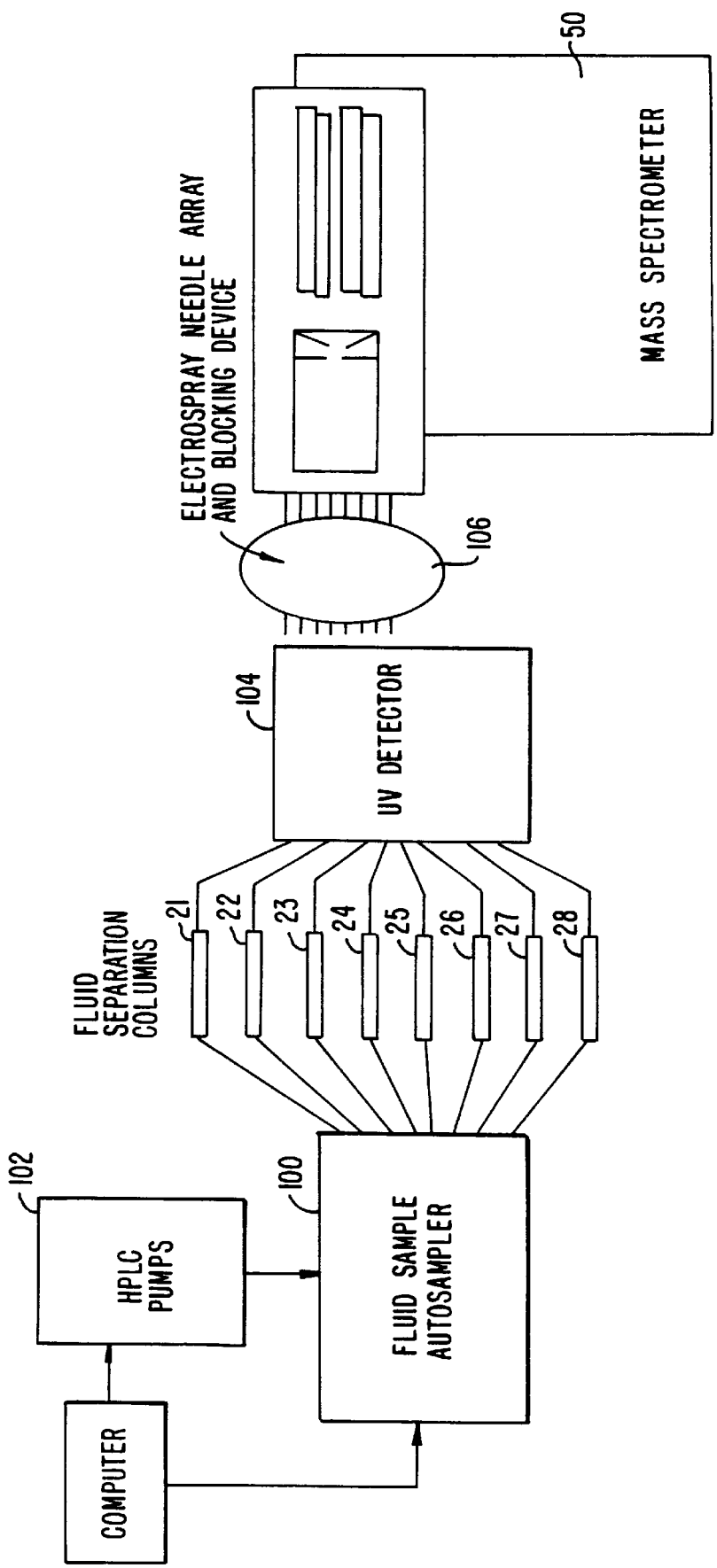
FIG. 7 is a schematic representation of a system similar to FIG. 6, but instead showing 8 fluid separation columns.
Figure 9:
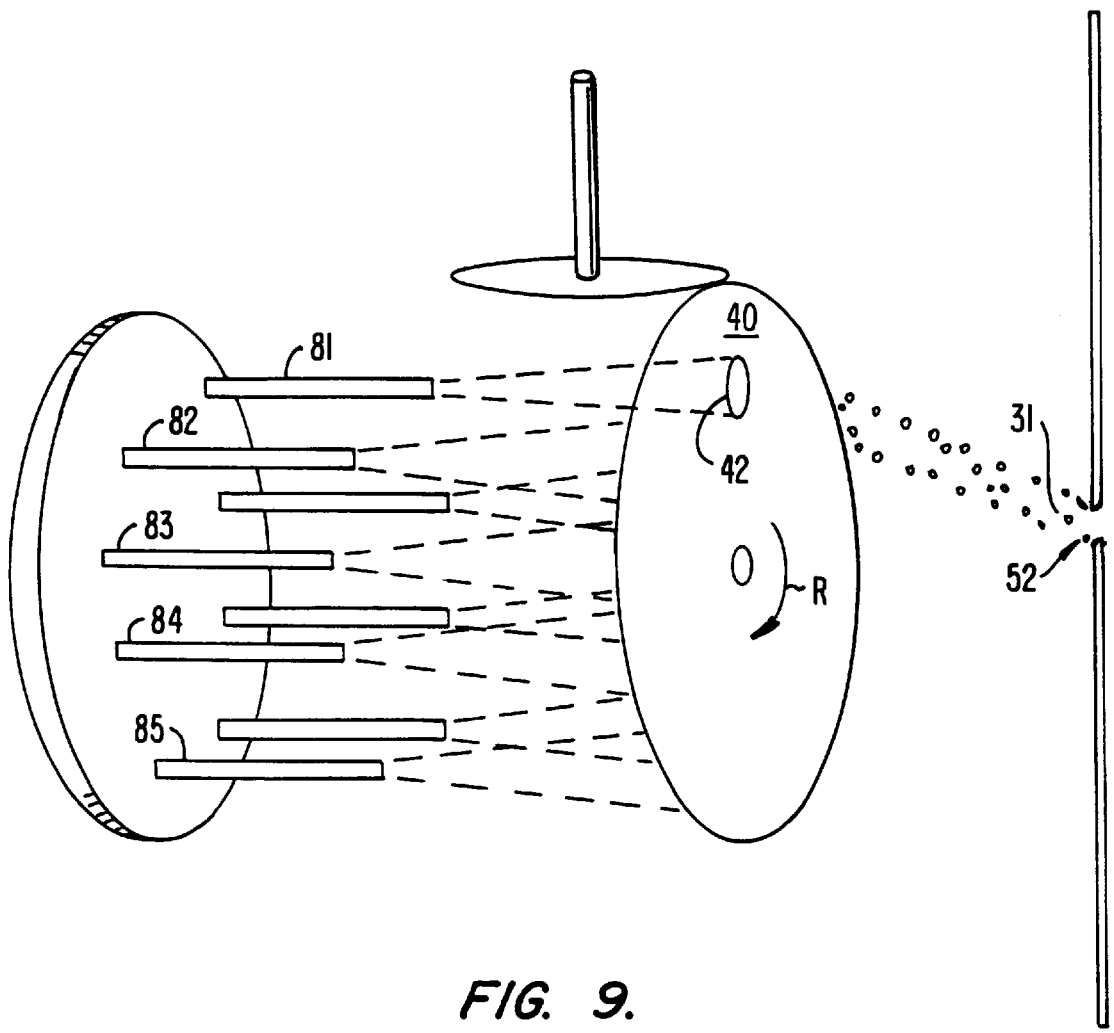
FIG. 9 is a perspective view of an eight column electrospray needle array, corresponding to the system of FIG. 7.
Figure 10:
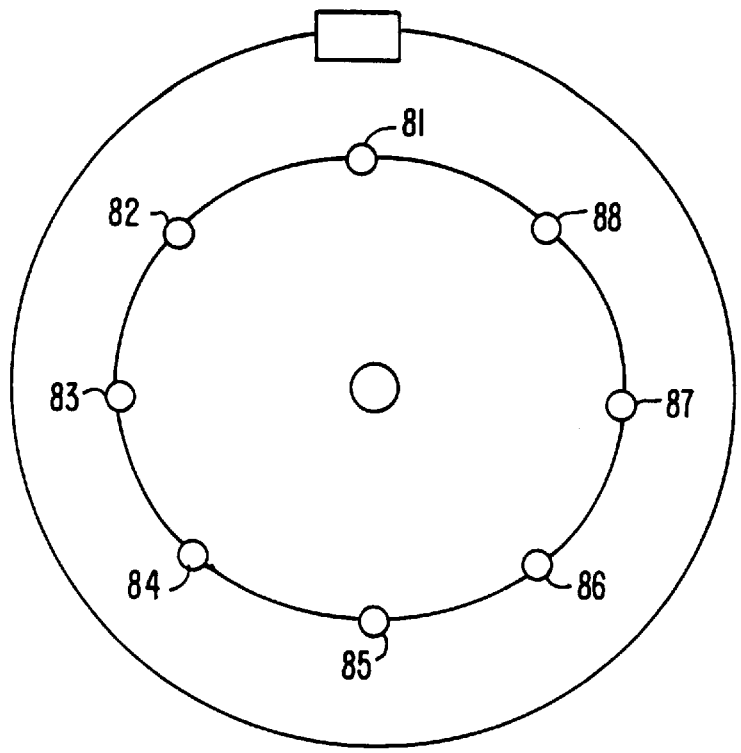
FIG. 10 is a front elevation view of the eight column electrospray needle array of FIG. 10.
Figure 11:
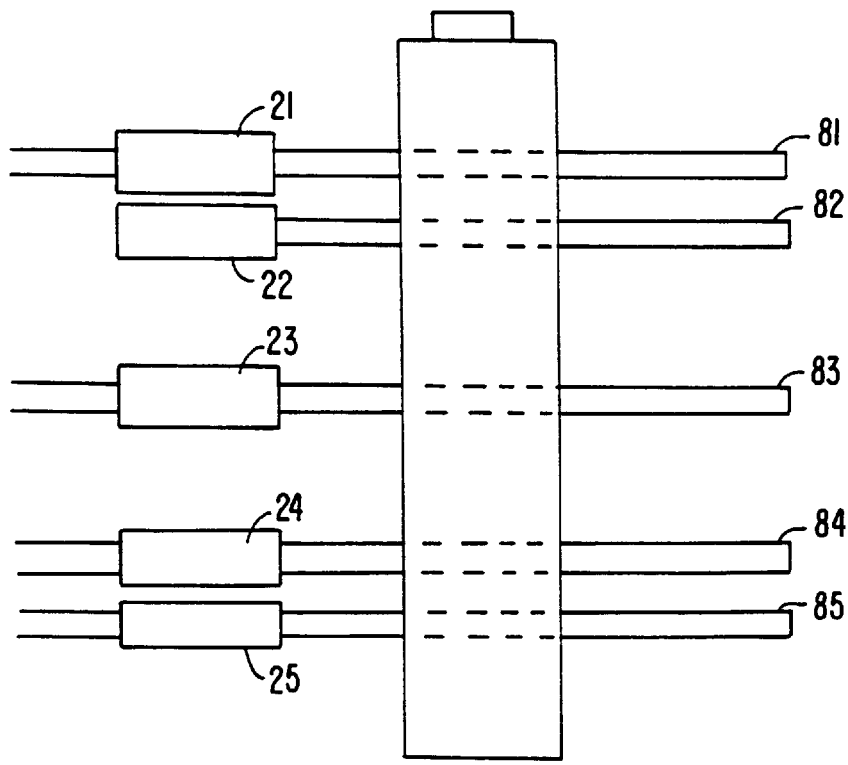
FIG. 11 is a side elevation view of the eight column electrospray needle array of FIG. 10.

The greater the number of columns in the system, the greater the number of fluid samples which can be simultaneously analyzed. FIGS. 1 to 6 show four fluid separation columns 21, 22, 23 and 24. It is to be understood that any plurality of columns may be used in the present invention. For example, FIG. 7 shows eight columns 21, 22, 23, 24, 25, 26, 27, 28, and FIGS. 9 to 11 show an electrospray needle array adapted for use with eight columns.

It is also to be understood that columns 21, 22, 23, 24, 25, 26, 27, and 28 may instead comprise flow injection transfer lines, capillary electrophoresis columns, supercritical fluid chromatography or any other system or device which can be used to direct a fluid sample into the entrance orifice of a mass spectrometer.

Returning to the exemplary system of FIGS. 1 and 2, each of columns 21, 22, 23 and 24 operate in parallel to separate fluid samples 11, 12, 13 and 14 into their respective component compounds which will elute out of the columns at different moments in time. The separated effluent passing out of columns 21, 22, 23 and 24 then passes into splitter tees 61, 62, 63 and 64, respectively, which are used to divert the majority of the HPLC effluent to dedicated fraction collectors, as will be described further herein. A small portion of the effluent passes out of the splitter tees, (typically less than 1%) and into the electrospray ionization region, (shown in detail in FIG. 5), whereby it is converted into fine, narrowly focussed aerosol electrosprays 31, 32, 33 and 34 respectively. A much larger portion, of the portion of the effluent is diverted from the splitter tees, (typically more than 99%), and is directed either to waste or to a dedicated fraction collector for compound isolation/purification, as will be explained. An advantage of requiring such a small amount of fluid to be dispensed as aerosol electrosprays 31, 32, 33 and 34 is conservation of fluid samples 11, 12, 13 and 14 for fraction collection.

As shown in FIG. 5, columns 21, 22, 23 and 24 are connected to electrospray needles 81, 82, 83 and 84, respectively. Together, electrospray needles 81, 82, 83 and 84 comprise an electrospray needle array 20. Electrospray needle array 20 preferably comprises either a single physical unit having a plurality of electrospray needles formed therein, or alternatively, array 20 may comprise a holding and targeting system for a plurality of separate conventional electrospray needles.

Fluid samples 11, 12, 13 and 14 are separated into their respective component compounds at the same time by liquid chromatography columns 21, 22, 23 and 24. Accordingly, effluent electrosprays 31, 32, 33, and 34 containing the separated compounds from each of the plurality of columns 21, 22, 23 and 24 are directed into the electrospray ionization region through a multiple electrosprayer device. Preferably, electrosprays 31, 32, 33 and 34 are directed in parallel with one another towards a rotating disc 40 which is positioned between the multiple electrospray needle array 20 and a mass spectrometer 50, as shown. Mass spectrometer 50 has an orifice plate 53 which preferably directs the ions formed in the aerosol electrosprays 31, 32, 33 and 34 into the mass spectrometer quadrupole region. Accordingly, electrosprays 31, 32, 33 and 34 are drawn toward opening 52, thus entering mass spectrometer 50. A skimmer 55 is provided to permit electrosprays 31, 32, 33 and 34 to enter the mass spectrometer, yet prevents other (neutral, un-ionized) particles from entering mass spectrometer 50. Should electrosprays 31, 32, 33 and 34 not be directed orthogonal to blocking device 40 as shown, ion optics can instead be used to focus electrosprays 31, 32, 33 and 34 into opening 52 of mass spectrometer 50.

Disc 40 has an off-center aperture 42 passing therethrough, as shown. Aperture 42 is preferably dimensioned to be of a size so as to permit only one of the simultaneously electrosprayed fluids to pass therethrough, for reasons to be explained. Therefore, disc 40 operates as a blocking device to prevent the passage of all but one of the fluid samples from entering opening 52 of mass spectrometer 50. For example, as can be seen in FIG. 1, spray 31 passes through aperture 42 and enters mass spectrometer 50 at the same moment in time when electrosprays 32, 33 and 34 are blocked by disc 40. Accordingly, mass spectrometer 50 generates a mass spectrum analysis of spray 31 as spray 31 is received therein thereby providing a compositional analysis of its corresponding fluid sample 11.

Preferably, electrosprays 31, 32, 33 and 34 are each targeted by electrospray needle array 20 such that they contact disc 40 at locations 38 which are all generally equidistant from center 44 of disc 42, as shown. Moreover, the distance from the center of aperture 42 to disc center 44 is also generally equidistant to the distance from locations 38 to disc center 44. Accordingly, as disc 40 is rotated in direction R from the first position as shown in FIG. 1 to the second position as shown in FIG. 2, aperture 42 will then be moved to align with electrospray 32 such that electrospray 32 enters mass spectrometer 50 while electrosprays 31, 33 and 34 are blocked, thus providing a mass spectral analysis of its corresponding fluid sample 12.

As can be appreciated, cyclical rotation of disc 40 will sequentially align aperture 42 with each of the locations 38 which correspond to each of electrosprays 31 to 34 such that electrosprays comprising fluid samples 11 to 14 will pass through aperture 42 in turn and enter mass spectrometer 50 one after another. A single complete rotation of disc 40 around its center 44 will result in a single mass spectrograph analysis being taken for each fluid sample. By moving disc 40 through multiple rotations, each fluid sample can be analyzed again and again in sequence over time.

Analysis of each of the electrosprays 31, 32, 33 and 34 at various moments in time permits a mass spectrometric reading to be generated for each fluid sample as the composition of the aerosol electrosprays 31, 32, 33 and 34 vary over time as the various component compounds in the respective fluid samples are separated and are eluted out of columns 21, 22, 23 and 24 at different periods of time.

Disc 40 can either be rotated at a continuous speed or in a series of quick jumps between electrosprays when aligning aperture 42 with each of the various electrosprays 31 to 34. Rotation at a continuous speed produces longer gaps of time between each of the electrosprays entering the mass spectrometer since any particular electrospray only passes through aperture 42 when the aperture is aligned with that particular electrospray. For example, during the period of time in which disc 40 is rotated from the position shown in FIG. 1 to the position in FIG. 2, all electrosprays will be temporarily blocked from passing therethrough when aperture 42 is positioned between electrosprays 31 and 32.

On the other hand, and preferably, rotating disc 40 in a series of quick jumps so as to rapidly align aperture 42 with each of the various electrosprays 31, 32, 33 and 34 has the advantage that each electrospray can be analyzed for a longer period of time during each rotation of the disc, as the periods of time during which all electrosprays are blocked by the disc is reduced. Advantages also occur when synchronizing the stepping of a quadrupole rod voltage with the rotation of disc 40 as will be explained.

Mass spectrometer 50 can comprise any type of mass spectrometry system, which may include, but are not limited to quadrupole and time-of-flight mass spectrometers, for reasons which will be explained.

By operating electrospray needle array 20 and disc 40 together with mass spectrometer 50, it is possible to determine the mass spectra of each of the fluid samples, while simultaneously spraying a plurality of separate fluid samples towards rotating disc 40 or other suitable blocking device, as follows.

Mass spectrometer 50 operates to generate a mass spectrum corresponding to the molecular masses which it senses to be present in the fluid sample spray which is received therein. Accordingly, in the absence of the present invention, should two or more fluid samples be simultaneously electrosprayed into mass spectrometer 50, the mass spectrometer will not, by itself, be able to differentiate between these various electrosprays so as to determine which compounds are present in each of the electrosprays. Instead, the two or more electrosprays would simultaneously enter and therefore be simultaneously analyzed by the mass spectrometer such that although a particular molecular mass presence could be detected, it would not be possible to attribute this molecular mass to one or the other of the fluid sample electrosprays.

In the present invention, mass spectrometer 50 is operated to continuously generate a mass spectrograph reading over a period of time during which each of the electrosprays 31, 32, 33 and 34 is sequentially received therein. By rotating disc 40 through a number of rotations, each electrospray will be separately analyzed a number of times. By knowing the position of rotating disc 40 with respect to electrospray needle array 20 at various moments in time, it is then possible to determine when each electrospray 31, 32, 33 and 34 passed through aperture 42, into opening 52, and was analyzed by mass spectrograph 50. The continuous mass spectrum reading generated by mass spectrometer 50 can then easily be sampled at those moments in time which correspond to when each of the electrosprays is analyzed in mass spectrometer 50. Thereby, a mass spectrum reading for each separate electrospray can be generated. By performing a mass spectrum analysis over a continuous period of time during which disc 40 is rotated around a number of times, it is then possible to determine a mass spectrum reading for each fluid sample 11, 12, 13 and 14 corresponding to electrosprays 31, 32, 33 and 34 at a number of different moments in time, thus yielding a time-based chromatographic and mass spectral analysis of each of the various fluid samples. Such a time-based chromatographic and mass spectral analysis permits monitoring of each fluid sample to determine the moments in time when each of the component compounds in the separated fluid samples is eluted out of its respective column.

For example, FIG. 8 shows an extracted ion chromatograph, being a graphical representation of mass spectrograph signals produced when operating the systems of FIGS. 1 or 2 over a short period of time. Specifically, peaks 91 correspond to the molecular weights of effluent of fluid sample 11 over a period of time. Similarly, peaks 92 correspond to the molecular weights of effluent of fluid sample 12 over a period of time, etc. As can be seen, each of samples 11, 12, 13, and 14 is sampled in a repetitive sequence. In the present invention, very rapid sampling can be achieved. For example, blocking device 40 may be positioned as shown in FIG. 1 for 100 msec, rotated to the position shown in FIG. 2 in 10 msec, and then remain at the position shown in FIG. 2 for 100 msec. Accordingly, each of the separated fluid samples eluted from the columns can be repetitively analyzed.

In a second preferred embodiment of the present invention, as seen FIG. 3, an electrospray needle array **20*b* is used in conjunction with a blocking plate 45 having an aperture 46 passing therethrough, as shown. Blocking plate 45 can be moved up or down in direction D1 as shown so as to selectively permit only one of the plurality of electrosprays 31 to 34, (in this illustration, spray 31), to enter the mass spectrometer 50. The operation of this second embodiment of the present invention is similar to that of the first embodiment, as described above, with the only substantial difference being that the blocking device comprises a blocking plate 45** which is moved back and forth in one direction, rather than being rotated around its center.

Keeping within the scope of the present invention, it is to be understood that blocking plate 45 may instead be held at a fixed position and electrospray needle array **20*b* can be moved up or down in direction D1 so as to sequentially permit each of the electrosprays 31 to 34 to pass through aperture 46 and enter mass spectrometer 50. It is also to be understood that various combinations of movement of both electrospray needle array 20*b* and blocking plate 45 can also be used to selectively permit electrosprays 31 to 34 to enter mass spectrometer 50** one after another.

In a third preferred embodiment of the present invention, as shown in FIG. 4, a non-rotating blocking device **40*b*** is equipped with a plurality of shutter valves 43 which can be individually selectively opened and closed so as to permit electrosprays 31 to 34 to enter mass spectrometer 50 one after another in turn. Valves 43 are preferably electronically controlled to selectively open and close one after another in turn, thereby permitting electrosprays 31 to 34 to enter mass spectrometer 50 in sequence. Accordingly, a blocking device comprising a rotating disc or translating plate is not required.

In another aspect of the invention, a method of purifying each of the fluid samples is provided. As used herein, "purifying" a fluid sample entails separating a fluid sample into its component compounds by liquid chromatography, and collecting that portion of the fluid sample which comprises a desired reaction compound in a sufficiently high concentration as the desired reaction compound is being eluted from a column. Accordingly, when purifying various fluid samples, expected molecular masses for each of these fluid samples will already be known and will be detected by the mass spectrometer, as follows.

When the system is positioned as shown in FIG. 1, the voltage across quadrupole rods 54 is preferably set to a voltage level corresponding to the molecular mass of a desired reaction compound expected to be present in electrospray 31. As the blocking device 40 is rotated to the position as shown in FIG. 2, the voltage across quadrupole rods 54 is preferably incrementally stepped to a voltage level corresponding to the molecular mass of a desired reaction compound expected to be present in electrospray 32. Preferably, the rotation of disc 40 and the stepping of voltage across quadrupole rods 54 is synchronized such that the voltage level is stepped at or near the moment in time when disc 40 is rotated from the position shown in FIG. 1 to the position shown in FIG. 2. A small lead time effect may be present necessitating stepping the voltage very shortly after rotation of the disc from a first position to a second position to compensate for the time delay of the electrospray physically reaching mass spectrometer 50 after passing through aperture 42.

An advantage of using incrementally stepped voltages is that mass spectrometer 50 searches only for the desired molecular masses expected to be found in each fluid sample and thus permits the analysis of each of the plurality of samples to be performed more rapidly. Consequently, using this method, a greater number of parallel fluid array HPLC columns may be accommodated in a given parallel analysis. For example, electrospray 31, (corresponding to fluid sample 11), is first analyzed at a first voltage corresponding to a first desired molecular mass to determine the concentration of such a first desired molecular mass therein. Electrospray 32, (corresponding to fluid sample 12), is then analyzed at a second voltage corresponding to a second desired molecular mass to determine the concentration of such a second desired molecular mass therein. The process is repeated such that each of the fluid samples is analyzed in turn at a voltage level unique to its desired molecular mass.

Another important advantage of purifying the desired (or expected) synthetic product of each of the electrosprays using the preferred method is that fraction collection, (in which the portion of the separated fluid sample having a sufficiently high concentration of a desired reaction compound is diverted to a fluid collector), can be provided as follows.

As is seen in FIG. 1, fraction collectors 37a, 37b, 37c and 37d are provided. It is to be understood that these fraction collectors may be physically separated from one another or alternatively, integrated into a single multi-chamber unit.

FIG. 1A is an enlarged view of the region encompassed by line 1A—1A in FIG. 1, showing fraction collection in microtitre plate format. Accordingly, in a preferred embodiment, the single multi-chamber unit can comprise a standard microtiter plate or plates such that purified or analyzed samples can be placed in a convenient liquid handling system format. As can be seen, fraction collector 37a is in fluid communication with fluid sample 11 by way of splitter tee 64. Tees 64 may each comprise Valco splitter tees which are configured to divert about 99% of the fluid eluted from the columns into the fraction collectors.

Referring to FIG. 1, when mass spectrometer 50 determines that a desired compound is present in separated electrospray 31 in a sufficiently high concentration, (as indicated by a high signal intensity), valve 38a is activated, sending the fluid into fraction collector 37a. At all other times, valve 38 is set to expel the fluid as waste W. As can be appreciated, fluid will pass out from tee splitters 61, 62, 63 and 64 into tubes 39 prior to electrosprays 31, 32, 33 and 34 actually reaching mass spectrometer 50. Accordingly, tubes 39 will preferably be fabricated of a length and diameter such that the partitioned fluid reaching valves 38 (typically more than 99% of the fluid eluted from the columns), will be identical in composition to the fluid simultaneously being analyzed by mass spectrometer 50 (typically less than 1% of the fluid eluted from the columns). In this way, the detection of a desired reaction compound in the fluid sample by the mass spectrometer will signal fraction collection to commence at the moment in time when such reaction compound reaches the fraction collection valve 38. Accordingly, any problems of time delay between detecting a desired reaction compound and collecting such reaction compound in a purified sample will be overcome by the present system.

Due to the rotation of disc 40, the each of the electrosprays 31, 32, 33 and 34 will be analyzed over and over again in sequence. Accordingly, fluid diversion into each of fluid collectors 37a–37d is performed precisely in time when mass spectrometer 50 determines the presence of desired reaction compounds therein to be of sufficient concentration. It is also to be understood that more than one fluid collector can be used for each fluid sample spray such that different desired compounds (which are eluted at different times from the same column), can be directed to different fluid collection chambers. This is preferably accomplished by having each of valves 38 set to direct fluid samples to a plurality of different fraction collectors. Accordingly, more than one desired reaction product can be purified for each fluid sample.

In another aspect of the invention, a method of analyzing each of the fluid samples so as to determine their composition is provided. As was set forth in the preferred method of analyzing the mass spectrum of a plurality of electrosprayed fluid samples, each of a plurality of fluid samples are electrosprayed in a manner so as to enter into a mass spectrometer 50 one after another. The present method of analyzing the mass spectrum of each fluid sample can be accomplished with the use of any type of mass spectrometer, including a quadrupole mass spectrometer, such as a PE-SCIEX API150 MCA Mass Spectrometer. However, the present invention is also particularly well suited for operation with a time of flight mass spectrometer, due to its ability to generate up to 10 full scan mass spectra per second. When analyzing fluid samples, as opposed to purifying fluid samples, it typically is not necessary to perform fraction collection. As such, the above described splitter tees and fraction collectors can be eliminated from the system.

When using a quadrupole mass spectrometer, the analysis of the composition of each of the fluid samples 11, 12, 13, and 14 is carried out with the voltage across quadrupole rods 54 being swept across a range of values as each electrospray 31, 32, 33 and 34 is analyzed in turn. For example, electrospray 31, (corresponding to fluid sample 11), is first analyzed with the voltage across the quadrupole rods being swept across a range to determine the composition of the fluid sample 11. Electrospray 32, (corresponding to fluid sample 12), is then analyzed with the voltage across the quadrupole rods being swept across a range to determine the composition of the fluid sample 12. The process is repeated such that each of the fluid samples is analyzed in turn.

Specifically, when the voltage level across quadrupole 54 corresponds to a molecular mass present in the electrospray, the presence of a reaction compound having this molecular mass will be detected as the quadrupole rods will allow ions in the electrospray having a molecular mass corresponding to the voltage to pass therethrough. As the quadrupole voltage is swept across the voltage range, a plurality of molecular masses (i.e.: reaction compounds), will be detected, and the composition of the particular electrospray will thereby be determined.

Figure 8:
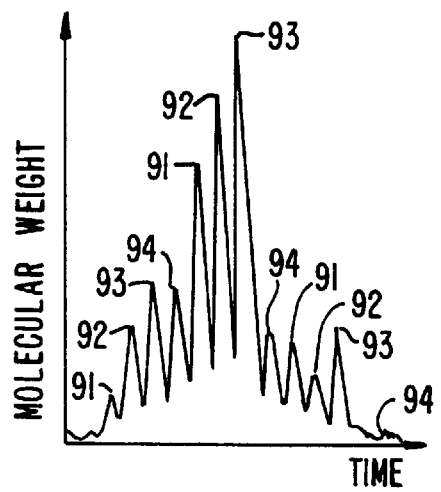
FIG. 8 is an example of an extracted ion chromatogram showing a graphical representation of mass spectrograph signals produced when operating the systems of FIGS. 1, 2, 3 or 4.

Preferably, the rotation of the disc is synchronized with the sweeping of the voltage across the quadrupole rods such that the disc is positioned (as in FIG. 1) to allow electrospray 31 to pass into mass spectrometer 50 while the voltage across quadrupole rods 54 is swept across a voltage range. Subsequently, disc 40 is rotated (as in FIG. 2) to allow electrospray 32 to enter mass spectrometer 50 with the voltage level again being swept across the voltage range. In this way, mass spectral analysis is sequentially performed on each fluid sample spray. By repeatedly rotating disc 40 around and around, the analysis of the mass spectra of each electrospray will be quickly repeated again and again. Consequently, as was described above with regard to FIG. 8, changes in the mass spectrograph of each electrospray can be monitored over time as different components of the sample are separately eluted from the columns.

Alternatively, when using a time-of-flight mass spectrometer, (which detects the presence of different molecular masses by determining the time taken for compounds having various molecular masses to pass through the flight tube of the spectrometer), the composition of each of the various fluid samples can also be analyzed in turn. An advantage of using time-of-flight mass spectrometer is that the electrosprays entering the mass spectrometer can be analyzed without requiring a considerable amount of time for the sampling of each electrospray. This is because it is not necessary to sequentially detect different molecular masses in each fluid sample by sweeping across a pre-set quadrupole voltage range. Rather, the plurality of different molecular masses are detected based upon their time-of-flight in each fluid sample as each fluid sample is analyzed in turn. Similarly, as was described above with regard to FIG. 8, changes in the mass spectrograph of each electrospray can be monitored over time as different components of the sample are separately eluted from the columns.

As is seen in FIG. 1, a computer 60 is also preferably included in the present invention. Computer 60 monitors mass spectrometer 50 and disc 40 such that, by knowing the position of aperture 42 with respect to columns 21, 22, 23 and 24, the distances between electrosprayer needle array 20, disc 40 and mass spectrometer 50, and the speed of the flow electrosprays 31, 32, 33 and 34, computer 60 thereby determines the moments in time at which each of fluid samples 31 to 34 is analyzed by mass spectrometer 50.

Accordingly, computer 60 can be used such that a continuous mass spectrum reading generated by mass spectrometer 50 can be deconvolutted using computer algorithms such that at particular moments in time the mass spectrum of each individual fluid sample can be determined.

The present system is ideally suited for use with microtiter reaction plates for parallel sample analysis, as follows. As stated above, fluid samples 11, 12, 13 and 14 can comprise fluid samples as deposited in individual wells in a microtiter plate. As seen in FIGS. 6 and 7, a fluid sample autosampler 100, which may comprise a Gilson 215 Eight Channel Injector, can be used to simultaneously draw samples from eight wells in a microtiter plate and, together with HPLC pumps 102, can be used to load the samples onto fluid separation columns (21, 22, 23, 24, 25, 26, 27, and 28 in FIG. 7). Accordingly, as is shown in FIGS. 7, 9, 10, and 11, eight fluid samples can be analyzed in parallel.

The present systems having four parallel electrospray heads, (FIGS. 1 to 6 and 8), and the systems having eight parallel electrospray heads, (FIGS. 7, and 9 to 11), are illustrative only in terms of the number of fluid samples. It is to understood that systems encompassing different numbers of parallel electrosprayers are also within the scope of the present invention.

When using an eight channel electrospray array as shown in FIGS. 9 to 11 with a standard 96 well microtiter plate, 12 sequential rows of 8 fluid samples can be analyzed or purified with the present invention. Specifically, after a first row of eight fluid samples have been simultaneously analyzed using the present system as set forth herein, a second row of reaction wells can be analyzed, etc. It is to be understood that different microtiter plate arrays can be used, including 48-well (6×8 arrays), 96-well (8×12 arrays), 384-well (15×24 arrays), etc.

As is shown in FIG. 7, should monitoring of ultraviolet properties of the fluid samples analyzed in parallel be also desired, an ultraviolet detector 104, which may comprise a Shimadzu SPD10AV UV Detector, can be positioned between columns 21, 22, 23, 24, 25, 26, 27, and 28 and the electrospray needle array and blocking device (seen in detail in FIGS. 1 to 5, and shown schematically here as 106).

What is claimed is:

1. A method of analyzing each of a plurality of fluid samples, comprising, simultaneously electrospraying a plurality of fluid samples from an electrospray needle array towards a mass spectrometer;

positioning a blocking device to block all but one of the fluid samples from reaching the mass spectrometer;

moving the electrospray needle array and blocking device relative to one another to permit the plurality of fluid samples to reach the mass spectrometer one at a time; and analyzing the mass spectrum of the plurality of fluid samples.

2. The method of claim 1, wherein positioning a blocking device comprises positioning the blocking device between the electrospray needle array and the mass spectrometer.

3. The method of claim 1, wherein moving the electrospray needle array and blocking device relative to one another comprises moving the blocking device in a cyclical manner such that each one of the plurality of fluid samples reaches the mass spectrometer one after another.

4. The method of claim 3, wherein positioning the blocking device comprises:

positioning a disc between the electrospray needle array and the mass spectrometer, the disc having an aperture passing therethrough; and simultaneously electrospraying each of the plurality of fluid samples towards the disc such that all but one of the plurality of fluid samples are blocked by the disc and one of the plurality of fluid samples passes through the aperture, thereby reaching the mass spectrometer.

5. The method of claim 4, wherein positioning the blocking device comprises:

electrospraying each of the fluid samples towards different locations on the disc, the different locations and the center of the aperture all being generally equidistant from the center of the disc.

6. The method of claim 5, further comprising:

rotating the disc, thereby permitting each of the fluid samples to pass one at a time through the aperture and thereby reach the mass spectrometer one at a time.

7. The method of claim 1, wherein analyzing comprises:

generating a continuous mass spectrum reading over a period of time; and sampling the continuous mass spectrum reading at moments in time when each fluid sample is analyzed; thereby generating a separate mass spectrum reading for each of the plurality of fluid samples over a period of time.

8. The method of claim 6, further comprising:

generating a continuous mass spectrum reading over a period of time; and sampling the continuous mass spectrum reading at moments in time when each fluid sample is analyzed; thereby generating a separate mass spectrum reading for each of the plurality of fluid samples over a period of time.

9. The method of claim 8 wherein the moments in time when each fluid sample is analyzed is determined by, determining the position of the aperture with respect to the electrospray needle array over a period of time, thereby determining when each fluid sample passes through the aperture and reaches the mass spectrometer.

10. The method of claim 8, wherein, generating a continuous mass spectrum reading comprises:

selecting a quadrupole mass spectrometer having quadrupole rods;

applying a voltage across the quadrupole rods; and incrementally stepping the voltage to levels corresponding to one or more molecular masses of component compounds in the plurality of fluid samples.

11. The method of claim 10, wherein the rotating of the disc and the stepping of the voltage across the quadrupole rods are synchronized such that the voltage is stepped when the fluid sample being analyzed is changed.

12. The method of claim 8, further comprising:

diverting a portion of at least one fluid sample to a fraction collector when a sufficient concentration of a selected component compound is detected in said at least one fluid sample.

13. The method of claim 8, wherein, generating a continuous mass spectrum reading comprises:

selecting a quadrupole mass spectrometer having quadrupole rods;

applying a voltage across the quadrupole rods; and sweeping the voltage across a voltage range.

14. The method of claim 13, wherein, the voltage is swept across the voltage range each time a sample is analyzed.

15. The method of claim 14, further comprising, determining the composition of each of the fluid samples by generating a mass spectrum reading for each fluid sample across the voltage range.

16. The method of claim 1, further comprising:

removing said plurality of fluid samples from separate wells in a microtiter reaction plate; and loading said plurality of fluid samples onto said electrospray needle array.

17. The method of claim 8, wherein said continuous mass spectrum reading is generated by a time-of-flight mass spectrometer.

18. A method of determining the composition of each of a plurality of fluid samples, comprising:

electrospraying a plurality of fluid samples from an electrospray needle array towards a mass spectrometer with all but one of the fluid samples being blocked by a rotating disc having an off-center aperture passing therethrough;

rotating the disc, thereby permitting each of the fluid samples to pass through the aperture and reach the mass spectrometer one at a time; and analyzing the mass spectrum of the fluid samples with the mass spectrometer, thereby determining the composition of each of the fluid samples.

19. A system for analyzing each of a plurality of fluid samples, comprising:

a mass spectrometer;

an electrospray needle array for spraying the plurality of fluid samples towards the mass spectrometer; and a blocking device positioned between the electrospray needle array and the mass spectrometer, the blocking device dimensioned to block all but one of the plurality of fluid samples from reaching the mass spectrometer, wherein the blocking device is movable with respect to the electrospray needle array so as to sequentially block each of the fluid samples from reaching the mass spectrometer.

20. The system of claim 19, wherein, the mass spectrometer is a quadrupole mass spectrometer.

21. The system of claim 19 wherein, the mass spectrometer is a time-of-flight mass spectrometer.

22. The system of claim 19, further comprising, a microcomputer for determining moments in time when each fluid sample reaches the mass spectrometer, and for sampling readings from the mass spectrometer at the moments in time when each fluid sample reaches the mass spectrometer, thereby determining a mass spectrum reading corresponding to each fluid sample over time.

23. The system of claim 19, further comprising, at least one fraction collector in fluid communication with one of the fluid samples.

24. The system of claim 23, wherein the at least one fraction collector comprises a microtiter reaction plate.

25. The system of claim 19, wherein, the electrospray needle array comprises, a shuttering valve mechanism for selectively permitting each fluid sample to be electrosprayed from one of the columns in the electrospray needle array.

26. A system for analyzing each of a plurality of fluid samples, comprising:

a mass spectrometer;

an electrospray needle array for spraying the plurality of fluid samples towards the mass spectrometer; and a blocking device positioned between the electrospray needle array and the mass spectrometer, the blocking device dimensioned to block all but one of the plurality of fluid samples from reaching the mass spectrometer wherein, the blocking device comprises a rotatable disc having an off-center aperture passing therethrough.

27. The system of claim 26, wherein, the electrospray needle array targets the plurality of fluid samples at different locations on the disc, the different locations and the center of the aperture all being generally equidistant from the center of the disc.

28. The system of claim 27, wherein, the disc is rotatable to permit each fluid sample to pass through the aperture and reach the mass spectrometer one at a time.

* * * * *